United States Patent

Nohira et al.

[11] Patent Number: 5,171,470
[45] Date of Patent: Dec. 15, 1992

[54] BIFUNCTIONAL OPTICALLY ACTIVE LIQUID CRYSTAL INTERMEDIATE COMPOUND, AND PROCESS FOR PREPARING SAME

[75] Inventors: Hiroyuki Nohira, 51-5,, Ohkuboryoke, Urawa-shi, Saitama-ken; Takahiro Ishizuka, Fujisawa; Kazuo Yoshinaga, Tokyo, all of Japan

[73] Assignees: Canon Kabushiki Kaisha; Hiroyuki Nohira, both of Tokyo, Japan

[21] Appl. No.: 563,698

[22] Filed: Aug. 7, 1990

[30] Foreign Application Priority Data

Aug. 8, 1989 [JP] Japan .................. 1-203932
Aug. 8, 1989 [JP] Japan .................. 1-203933
Jul. 23, 1990 [JP] Japan .................. 1-192927

[51] Int. Cl.$^5$ .............. C09K 19/06; C09K 19/52; C07C 41/00
[52] U.S. Cl. .............. 252/299.6; 252/299.01; 568/642; 568/647; 568/897
[58] Field of Search ......... 252/299.01, 299.6; 568/642, 643

[56] References Cited

U.S. PATENT DOCUMENTS 4,560,811 12/1984 Sharpless et al. ............. 568/848
4,798,680 1/1989 Nohira et al. ............. 252/299.01
4,801,759 1/1989 Siegmeier et al. ............. 568/833
4,918,213 4/1990 Nohira et al. ............. 558/271

OTHER PUBLICATIONS

Morrison & Boyd, Organic Chemistry, pp. 715–716, 133, 158–160 5th Edition.
Chemical Abstracts 100:22830f.
Chemical Abstracts 54:6678.

*Primary Examiner*—Robert L. Stoll
*Assistant Examiner*—Cynthia Harris
*Attorney, Agent, or Firm*—Fitzpatrick, Cella, Harper & Scinto

[57] ABSTRACT

A bifunctional optically active liquid crystal intermediate compound represented by the following Formula (I): X—Y—C*H(M)—CH$_2$—OH is disclosed, wherein X represents CH$_2$=CH—, HOCH$_2$—CH$_2$—, HSCH$_2$—CH$_2$—, HOCH$_2$—, HOOC—, HOCH$_2$CH=CH—, CH$_3$CH(OH)— or HOCH$_2$C*H(Z)—; Y represents $-(CH_2)_n-$ or $-((CH_2)_m-O-)_l-CH_2-$, where n represents an integer of 1 to 18, m represents an integer of 1 to 12, and l represents an integer of 1 to 4; M and Z each represents halogen atom, an alkyl group or an alkoxy group, said halogen atom being selected from the group consisting of I, Cl, Br and F, and said alkyl group or alkoxy group having 1 to 8 carbon atoms; and the mark * represents an asymmetric carbon atom. A process for preparing the intermediate compound is also disclosed.

8 Claims, No Drawings

BIFUNCTIONAL OPTICALLY ACTIVE LIQUID CRYSTAL INTERMEDIATE COMPOUND, AND PROCESS FOR PREPARING SAME

BACKGROUND OF THE INVENTION

1. Field of the Invention

The present invention relates to a bifunctional optically active liquid crystal intermediate compound useful as an intermediate for synthesizing a liquid crystal or polymeric liquid-crystal compound, and a process for preparing it.

More particularly the present invention is concerned with a liquid crystal intermediate compound used as an optically active component in a chiral nematic liquid crystal or a chiral polymeric liquid-crystal compound and a chiral smectic liquid crystal or a chiral polymeric liquid-crystal compound which are characterized as being optically active.

2. Related Background Art

Hitherto known liquid-crystal devices include a device that employs the twisted nematic liquid crystal as disclosed in M. Schadt and W. Helfrich, Voltage Dependent Optical Activity of a Twisted Nematic Liquid Crystal, "Applied Physics Letters", Vol. 18, No. 4, pp. 127–128 (Feb. 15, 1971). This twisted nematic liquid crystal, however, has a problem of crosstalk occurring at the time of time division drive using a matrix electrode system having a high density of picture elements, and hence has a restriction in the number of the picture elements.

There has been also a limit in its use as a display device because of a slow electric field response and poor visual-field angle characteristics. This liquid crystal has another problem that a very complicated process is required for the formation of a thin-film transistor for each picture element and moreover a display device with a large area can be produced with difficulty.

For eliminating the disadvantages of such a conventional liquid-crystal device, Clark and Lagewall have proposed to use a liquid-crystal device comprised of a bistable element (see Japanese Patent Application Laid-Open No. 56-107216 and U.S. Pat. No. 4,367,924). Commonly used as this liquid crystal comprised of a bistable element is a ferroelectric liquid crystal comprised of a chiral smectic C phase (Sm*C) or H phase (Sm*H).

This ferroelectric liquid crystal (FLC) exhibits spontaneous polarization, and hence has a very quick response and moreover can produce a bistable state with memory performance. In addition, it has superior visual-field angle characteristics, and hence can be considered to be suited as a material for display with a large capacity and a large area. When, however, a liquid crystal cell is actually formed, it is difficult to achieve a monodomain over a large area, and a technical problem has remained unsettled in making a display device with a large screen.

As a countermeasure to such problems, it is reported in U.S. Pat. No. 4,561,726 to utilize an interfacial surface energy so that a monodomain of a ferroelectric smectic liquid crystal can be prepared by an epitaxial method.

The monodomain thus prepared, however, can not be stable by nature and may easily turn into a multidomain by the application of pressure or thermal stimulation. This makes it difficult to accomplish large-area display.

On the other hand, a polymeric liquid-crystal device has been proposed as a device that can be readily fabricated as a device and is suited for large-area display. The device as disclosed in U.S. Pat. No. 4,239,435 is known as a device driven by the application of an electric field.

What is disclosed in British Patent No. 2,146,787 is known as a device that can be addressed using a laser beam. Japanese Patent Application Laid-Open No. 62-14114 discloses a device that can be addressed using a thermal head or the like.

Of these devices, the device employing a chiral nematic polymeric liquid crystal containing an optically active group performs display and recording in a wavelength-selective state by the use of spiral selective scattering of the polymeric liquid crystal.

Display units that employ such polymeric liquid-crystal devices are suited for highly detailed display with large areas, but are disadvantageous in that they have too low response speed to be suitable for animations or for uses in which rewriting is performed at a high speed.

Various studies are made for the purpose of eliminating the above disadvantages. As one of the results thereof, a ferroelectric polymeric liquid crystal is reported in N. A. Platé et al., Polymer Bulletin, 12, p.299 (1984). This ferroelectric polymeric liquid crystal can be readily formed into a device, e.g., readily formed into a film, and is suited for large-area display. This can greatly improve response speed compared with a conventional polymeric liquid crystal, and can be expected to be put into practical use.

In the manufacture of such a ferroelectric polymeric liquid crystal, it is essential to use an optically active compound. For example, an optically active alcohol or an optically active carboxylic acid is used as the optically active compound.

Of these optically active compounds, a monofunctional optically active liquid crystal intermediate is the same as the one used in a low-molecular liquid crystal, and can be used in a terminal side chain of a polymeric liquid crystal. It, however, can not be used in a spacer flexible chain of a main-chain type polymeric liquid crystal or in a side-chain spacer flexible chain of a side-chain type polymeric liquid crystal. Hence, the polymeric liquid crystal produced using a monofunctional optically active liquid crystal intermediate has the disadvantage that it must be limited in structure.

On the other hand, bifunctional optically active liquid crystal intermediate compounds hitherto known are few in kind and limited in structure, and hence there has been the disadvantage that the liquid crystal or polymeric liquid crystal produced using the intermediate compound is also limited in structure for its molecular designing. In addition, the bifunctional optically active liquid crystal intermediate compound is expensive and has allowed no free selection on its length (or the number of carbon atoms) when used as a flexible spacer chain of a polymeric liquid crystal.

Moreover, none of the conventional bifunctional optically active liquid crystal intermediate compounds have a large permanent dipole moment in the vicinity of an asymmetric atom. Hence, they exhibit a small spontaneous polarization when formed into ferroelectric polymeric liquid crystals or polymeric liquid crystals, and have had the disadvantage that a high-speed response can be achieved with difficulty.

SUMMARY OF THE INVENTION

An object of the present invention is to provide a bifunctional Optically active liquid crystal intermediate compound that can eliminate the above disadvantages of the conventional optically active liquid crystal intermediate compounds, has a large permanent dipole moment near an asymmetric atom, and is capable of changing its length as a flexible spacer chain, and also provide a process for preparing such a compound.

The present invention provides an optically active compound represented by the following Formula (I):

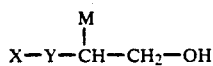
(I)

wherein
X represents $CH_2=CH-$, $HOCH_2-CH_2-$, $HSCH_2-CH_2-$, $HOCH_2-$,

$HO-CH_2-CH=CH-$,

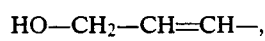

Y represents $-(CH_2)_n-$ or $-((CH_2)_m-O)_l-CH_2-$, where n represents an integer of 1 to 18, and preferably 1 to 12, m represents an integer of 1 to 12, and preferably 1 to 9, and l represents an integer of 1 to 4, and preferably 2 to 4; M and Z each represents a halogen atom, an alkyl group or an alkoxy group, said halogen atom being selected from the group consisting of I, Cl, Br and F, and said alkyl group or alkoxy group having 1 to 8 carbon atoms; and the mark * represents an asymmetric carbon atom.

In particular, the present invention provides a bifunctional optically active liquid crystal intermediate compound represented by the following Formula (I-1):

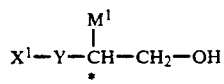
(I-1)

wherein
$X^1$ represents $CH_2=CH-$, $HOCH_2-CH_2-$,

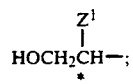

Y represents $-(CH_2)_n-$ (n=1 to 18) or $-((CH_2)_m-O)_l-CH_2-$ (m=1 to 12, l=1 to 4); $M^1$ and $Z^1$ may be the same or different and each represents a halogen atom; and the mark * represents an asymmetric carbon atom.

The present invention also provides a process for preparing a bifunctional optically active liquid crystal intermediate compound, comprising allowing an optically active epoxide compound represented by Formula (II-1):

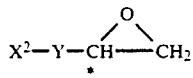
(II-1)

wherein
$X^2$ represents $CH_2=CH-$, $HOCH_2-CH_2-$,

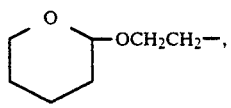

$HO-CH_2-CH=CH-$,

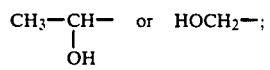

Y represents by $-(CH_2)_n-$ (n=1 to 18) or $-((CH_2)_m-O)_l-CH_2-$ (m=1 to 12, l=1 to 4); and
the mark * represents an asymmetric carbon atom;
to react with a compound represented by HM or $M_3Al$, where M represents a halogen atom, an alkyl group or an alkoxy group, to form a compound represented by the following Formula (I-2):

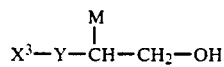
(I-2)

wherein
$X^3$ represents $CH_2=CH-$, $HOCH_2-CH_2-$, $HSCH_2-CH_2-$, $HOCH_2-$,

$HO-CH_2-CH=CH-$ or

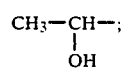

Y and M are as defined above; and
the mark * represents an asymmetric carbon atom.

The present invention further provides a process for preparing a bifunctional optically active liquid crystal intermediate compound, comprising allowing an optically active diepoxide compound represented by Formula (II-2):

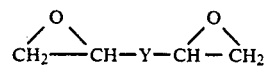
(II-2)

wherein Y represents by $-(CH_2)_n-$ (n=1 to 18) or $-((CH_2)_m-O)_l-CH_2-$ (m=1 to 12, l=1 to 4); and the mark * represents an asymmetric carbon atom
to react with one or two compounds selected from a compound represented by HZ, $Z_3Al$, HM or $M_3Al$, where M and Z each represents a halogen atom, an alkyl group or an alkoxy group, to form a compound represented by the following Formula (I-3).

$$\underset{*}{HOCH_2\overset{Z}{\underset{|}{C}}H}-Y-\underset{*}{\overset{M}{\underset{|}{C}}HCH_2OH} \quad (I\text{-}3)$$

wherein,

M, Y and Z are as defined above; M and Z may be the same or different; and the mark * represents an asymmetric carbon atom.

DETAILED DESCRIPTION OF THE PREFERRED EMBODIMENTS

The present invention will be described below in detail.

The process for preparing the bifunctional optically active liquid crystal intermediate compound of the present invention provides an optically active compound represented by the following Formula (I).

$$X-Y-\underset{*}{\overset{M}{\underset{|}{C}}H}-CH_2-OH \quad (I)$$

In the above Formula (I), X represents $CH_2=CH-$, $HOCH_2-CH_2-$, $HSCH_2-CH_2-$, $HOCH_2-$, $HO-CH_2-CH=CH-$, $CH_3-\underset{OH}{\underset{|}{C}}H-$ or $\underset{*}{HOCH_2\overset{Z}{\underset{|}{C}}H}-$.

Y represents $-(CH_2)_n-$ or $-((CH_2)_m-O)_l-CH_2-$, where n represents an integer of 1 to 18, and preferably 1 to 12, m represents an integer of 1 to 12, and preferably 1 to 9, and l represents an integer of 1 to 4, and preferably 2 to 4. M and Z each represents a halogen atom, an alkyl group or an alkoxy group. The halogen atom represented by M and Z is selected from the group consisting of I, Cl, Br and F, and the alkyl group or alkoxy group may preferably be those having 1 to 8 carbon atoms. The mark * represents an asymmetric carbon atom.

The bifunctional liquid crystal intermediate compound comprising the optically active compound represented by the above Formula (I) can be derived from and synthesized using as a starting material an optically active epoxide compound represented by the following Formula (II-1).

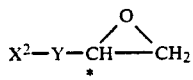  (II-1)

In Formula (II-1), $X^2$ represents $CH_2=CH-$, $HOCH_2-CH_2-$,

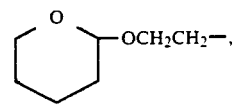

$HO-CH_2-CH=CH-$, $CH_3-\underset{OH}{\underset{|}{C}}H-$ or $HOCH_2-$.

Y is a flexible spacer, representing the same as defined above. The mark * represents an asymmetric carbon atom.

The optically active epoxide compound represented by the above Formula (II-1) can be obtained by microbial oxidation of an olefin, as disclosed in K. Furuhashi et al., European journal of Microbiology and Biotechnology (Eur. J. Appl. Microbiol. Biotechnol.), 12, p.39, 1981, or asymmetrical epoxidation, as disclosed in T. Katsuki and K. B. Sharpless, Journal of American Chemical Society (J. Am. Chem. Soc.), 102, p.5974, 1980.

Specific structures of the optically active epoxide compound represented by Formula (II-1) include the following, which, however, are by no means limited to these.

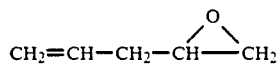

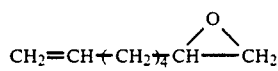

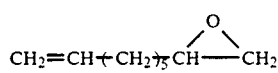

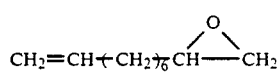

The above optically active epoxide compound may be allowed to react with a compound represented by HM or $M_3Al$ (wherein M represents a halogen atom, an alkyl group or an alkoxy group). The bifunctional optically active liquid crystal intermediate compound can be thus produced. The following are typical examples of the reaction by which the bifunctional optically active liquid crystal intermediate compound of the present invention is derived from the above chiral epoxide.

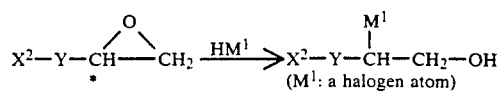
($M^1$: a halogen atom)

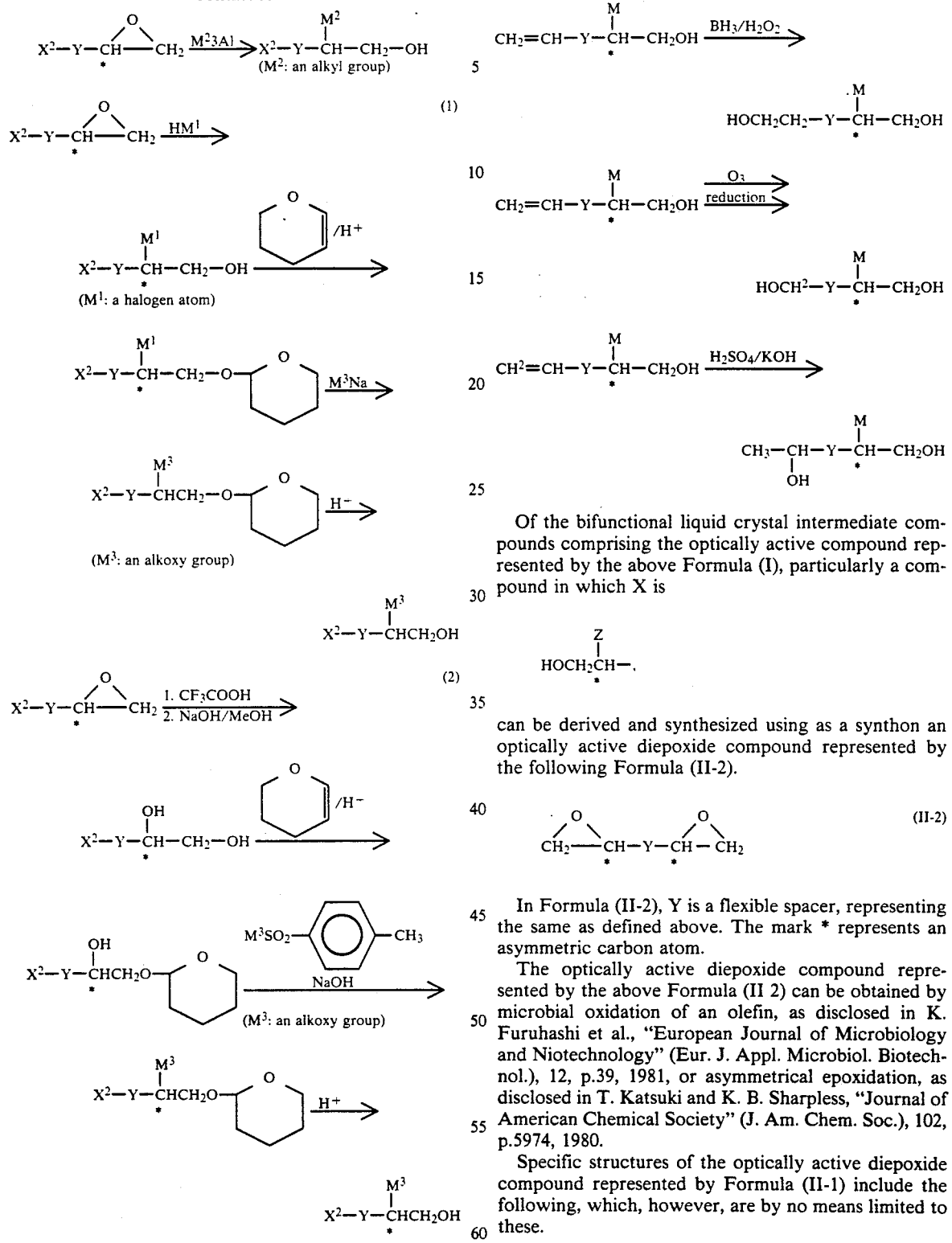

In instances in which $X^2$ of the bifunctional optically active liquid crystal intermediate compound is different from the X as previously defined, the compound can be derived to another bifunctional optically active liquid crystal intermediate compound through the reaction as shown below.

Of the bifunctional liquid crystal intermediate compounds comprising the optically active compound represented by the above Formula (I), particularly a compound in which X is $$HOCH_2CH-\overset{Z}{\underset{*}{|}}$$

can be derived and synthesized using as a synthon an optically active diepoxide compound represented by the following Formula (II-2).

In Formula (II-2), Y is a flexible spacer, representing the same as defined above. The mark * represents an asymmetric carbon atom.

The optically active diepoxide compound represented by the above Formula (II 2) can be obtained by microbial oxidation of an olefin, as disclosed in K. Furuhashi et al., "European Journal of Microbiology and Niotechnology" (Eur. J. Appl. Microbiol. Biotechnol.), 12, p.39, 1981, or asymmetrical epoxidation, as disclosed in T. Katsuki and K. B. Sharpless, "Journal of American Chemical Society" (J. Am. Chem. Soc.), 102, p.5974, 1980.

Specific structures of the optically active diepoxide compound represented by Formula (II-1) include the following, which, however, are by no means limited to these.

-continued

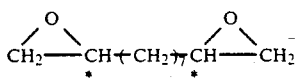

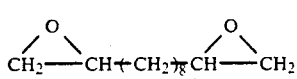

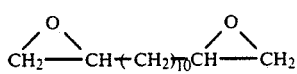

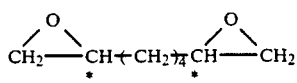

-continued

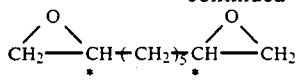

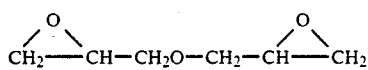

The above optically active epoxide compound may be allowed to react with one or two compounds selected from a compound represented by HZ, $Z_3Al$, HM or $M_3Al$, (wherein M and Z each represent a halogen atom, an alkyl group or an alkoxy group). The bifunctional optically active liquid crystal intermediate compound can be thus produced. The following are typical examples of the reaction by which the bifunctional optically active liquid crystal intermediate compound of the present invention is derived from the above chiral diepoxide.

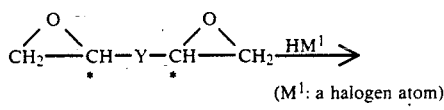

($M^1$: a halogen atom)

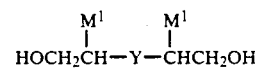

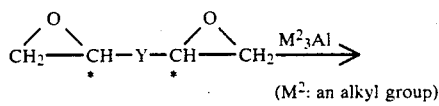

($M^2$: an alkyl group)

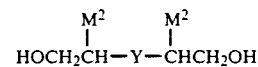

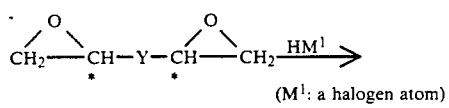

($M^1$: a halogen atom)

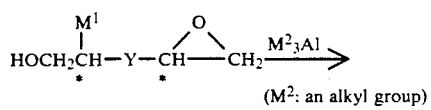

($M^2$: an alkyl group)

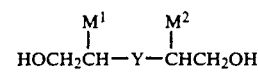

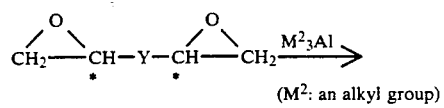

($M^2$: an alkyl group)

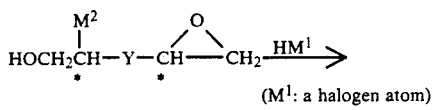

($M^1$: a halogen atom)

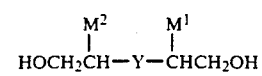

-continued (1)

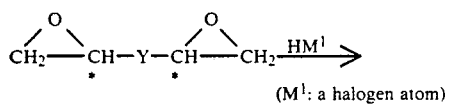
(M¹: a halogen atom)

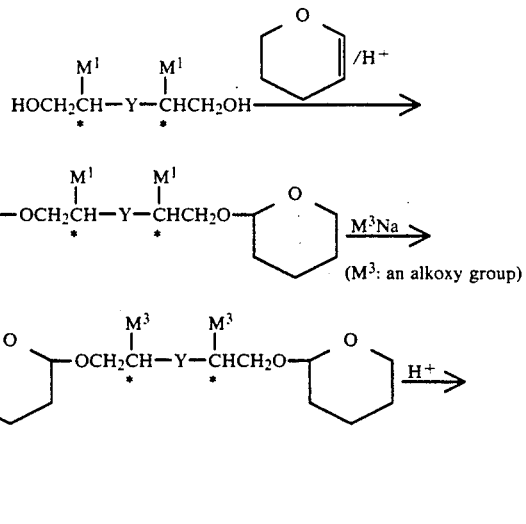

(2)

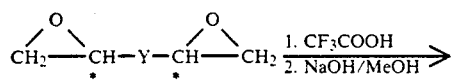

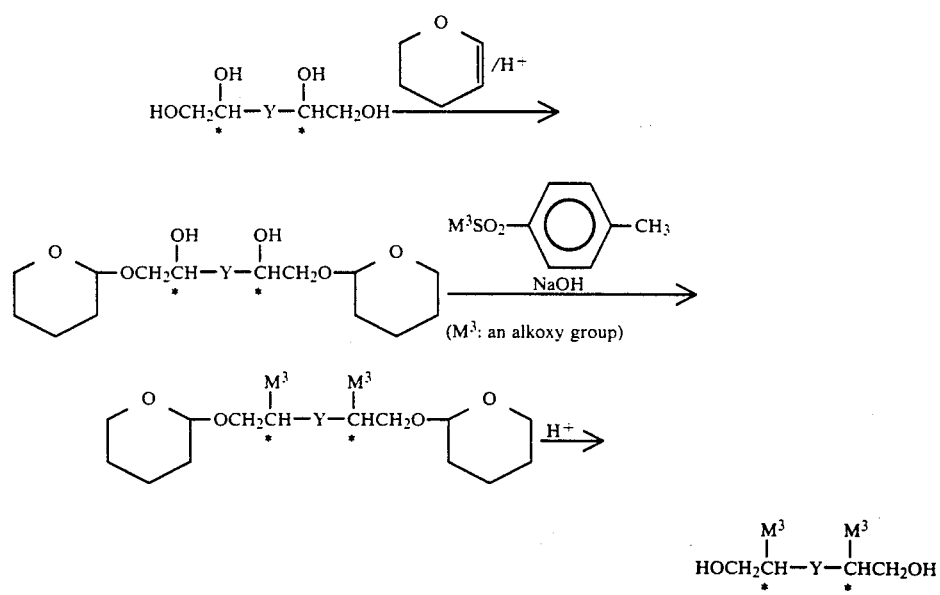

The bifunctional optically active liquid crystal intermediate compound obtained through the reaction described above may be reacted with a bifunctional mesogen group to form an ester bond, ether bond, thioester bond or thioether bond, and thus a polymeric liquid-crystal compound can be derived.

When a polymeric liquid-crystal compound is produced using the bifunctional optically active liquid crystal intermediate compound of the present invention, the resulting polymeric liquid crystal compound can have a large permanent dipole moment near an asymmetric atom and is capable of changing its length as a flexible spacer chain.

In particular, the compound wherein the M in the above Formula (I) is a halogen atom can be a compound having a large polarity.

EXAMPLES

The present invention will be described below in greater detail by giving Examples.

EXAMPLE 1

Synthesis of 2-fluoro-9-decen-1-ol

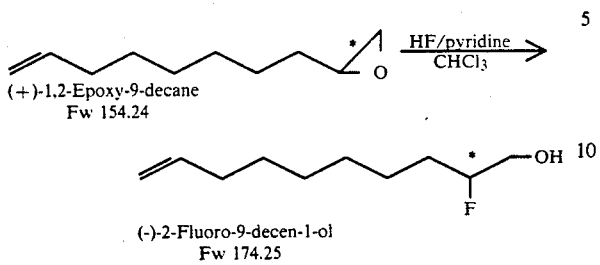

In an Erlenmeyer flask made of a plastic, 0.45 ml of hydrogen fluoride/pyridine was put, and 1 ml of chloroform as a solvent was added thereto. The mixture was cooled to −20° C. with dry ice/ethanol, and a 3 ml chloroform solution of 308 mg (2 mmol) of (+)-1,2-Epoxy-9-decene was dropwise added thereto. The mixture was further stirred at 0° C. for 3.5 hours. After completion of the reaction, 2 ml of pyridine was added and then 4 ml of an aqueous 6N NaOH solution was slowly dropwise added to neutralize the hydrogen fluoride. To the resulting reaction mixture, 2 g of anhydrous sodium carbonate was added, and the organic layer was separated, followed by washing with 3 ml of 6N HCl, subsequently 3 ml of 3N HCl and 3 ml of a saturated aqueous sodium hydrogencarbonate solution, and then drying with anhydrous magnesium sulfate.

After evaporation of the solvent, micro-distillation was carried out to give 143 mg (0.82 mmol) of 2-fluoro-9-decen-1-ol. (41% yield, 35 mmHg, 150° C.)

Specific rotation of the product:

$[\alpha]_D^{28}$ −10.0,    $[\alpha]_{435}^{26}$ −18.3
(c = 0.52, Et$_2$O)

EXAMPLE 2

Synthesis of 2-fluoro-1,10-decanediol

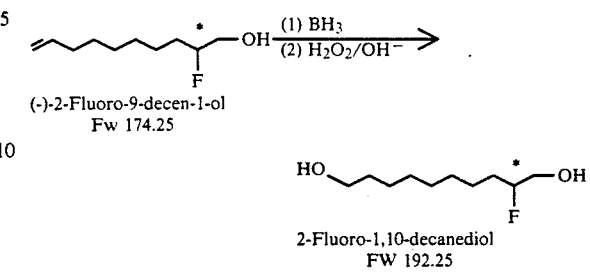

In 6 ml of dried THF, 585 mg (3.36 mmol) of the substrate (−)-2-fluoro-9-decen-1-ol was dissolved, and the solution was kept ice-cooled. Into the resulting solution, diborane prepared by dropwise adding 0.78 g (5.5 mmol) of a boron trifluoride ether complex to a 6 ml dried diglyme solution of 189 mg (5 mmol) of sodium borohydride was blown (for about 10 minutes). With further stirring at room temperature, the reaction mixture turned into a gel with progress of the reaction. After it was left to stand for 30 minutes, 0.5 ml of distilled water was dropwise added, followed by addition of 3 ml of an aqueous 3N sodium hydroxide solution and 3 ml of 30% hydrogen peroxide water. The reaction mixture was stirred for 30 minutes, sodium chloride was added, and the organic layer was taken out. Extraction from the aqueous layer was carried out twice using 2 ml of ethyl ether, and the extract was dried with anhydrous magnesium sulfate together with the organic layer previously taken out, followed by micro-distillation to give 493 mg (2.56 mmol) of 2-fluoro-1,10-decanediol. (0.7 torr, 170° to 190° C., 76% yield)

Specific rotation of the product:

$[\alpha]_D^{26}$ −3.9,    $[\alpha]_{435}^{25}$ −8.4
(c = 0.92, MeOH)

EXAMPLES 3 to 6

Using starting materials epoxy alkenes as shown below, syntheses were carried out in the same manner as in Example 1 to give fluoroalkene alcohols. Specific rotations of the resulting products are shown below.

| Example | Starting material | Specific rotation $[\alpha]_D^{28}$ |
|---|---|---|
| 3 | CH$_2$=CH⁺CH$_2$)$_4$CH——CH$_2$ (with epoxide O) | −11.4 (c = 1.1, Et$_2$O) |
| 4 | CH$_2$=CH⁺CH$_2$)$_5$CH——CH$_2$ (with epoxide O) | −10.9 (c = 018, Et$_2$O) |
| 5 | CH$_2$=CH⁺CH$_2$)$_9$CH——CH$_2$ (with epoxide O) | −8.2 (c = 0.5, Et$_2$O) |
| 6 | CH$_2$=CH—CH$_2$—O—CH$_2$—CH——CH$_2$ (with epoxide O) | −13.0 (c = 1.0, Et$_2$O) |

EXAMPLES 7 to 9

Using the fluoroalkene alcohols of Examples 3 to 5, syntheses were carried out in the same manner as in Example 2 to give the fluoroalkane diols. Specific rotations of the resulting products are shown below.

| Example | Starting material | Specific rotation $[\alpha]_D^{28}$ |
|---|---|---|
| 7 | $\underset{*}{CH_2=CH(CH_2)_4CHCH_2OH}$ with F | −4.6 (c = 0.8, MeOH) |
| 8 | $\underset{*}{CH_2=CH(CH_2)_5CHCH_2OH}$ with F | −4.1 (c = 0.5, MeOH) |
| 9 | 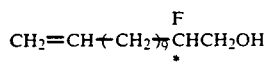 | −3.0 (c = 0.5, MeOH) |

$$\underset{*}{CH_2=CH(CH_2)_{10}CHCH_2OH} \text{ with F}$$

EXAMPLE 10

Synthesis of 2,9-difluoro-1,10-decanediol by cleavage reaction of an epoxy

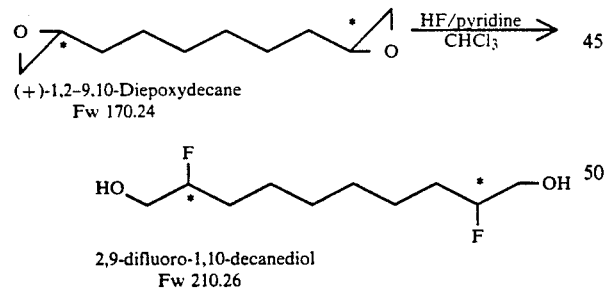

(+)-1,2-9,10-Diepoxydecane
Fw 170.24

2,9-difluoro-1,10-decanediol
Fw 210.26

In an Erlenmeyer flask made of a plastic, 851 mg (5 mmol) of (+)-1,2-9,10-diepoxydecane and 20 ml of of chloroform were added. The mixture was cooled to −20° C. with dry ice/ethanol. While the mixture was thoroughly stirring, 1.7 ml of hydrogen fluoride/pyridine was dropwise added. After reaction at 0° C. to room temperature for 4 hours, the reaction mixture was cooled to −10° C., followed by addition of 2 ml of pyridine and 2.5 ml of 6N NaOH. The organic layer was decanted, and then extraction from the NaF-aqueous layer was carried out three times with 5 ml of ether. The chloroform layer and the ether extract were combined, followed by washing with 5 ml of 3N NaOH, 6N HCl, 10% NaHCO₃ and distilled water, and then drying with anhydrous magnesium sulfate.

After evaporation of the solvent, micro-distillation was carried out to give 123 mg (0.58 mmol) of 2-9-difluoro-1,10-decanediol. (White solid, m.p. 104° to 107° C., b.p. 130° to 140° C./0.6 torr)

Specific rotation of the product:

$$[\alpha]_D^{26} -10.1, \quad [\alpha]_{435}^{24} -18.8$$
$$(c = 1.29, MeOH)$$

EXAMPLES 11 to 13

Using starting materials diepoxy alkanes as shown below, syntheses were carried out in the same manner as in Example 1 to give difluorodiols. Specific rotations of the resulting products are shown below.

| Example | Starting material | Specific rotation $[\alpha]_D^{28}$ |
|---|---|---|
| 11 | $\underset{*}{CH_2}\!-\!\overset{O}{\overset{\diagup\diagdown}{CH}}\!(CH_2)_4\underset{*}{CH}\!-\!\overset{O}{\overset{\diagup\diagdown}{CH_2}}$ | −11.5 (c = 0.7, MeOH) |
| 12 | $\underset{*}{CH_2}\!-\!\overset{O}{\overset{\diagup\diagdown}{CH}}\!(CH_2)_{10}\underset{*}{CH}\!-\!\overset{O}{\overset{\diagup\diagdown}{CH_2}}$ | −7.9 (c = 0.5, MeOH) |
| 13 | $CH_2\!-\!\overset{O}{\overset{\diagup\diagdown}{CH}}\!-\!CH_2\!-\!O\!-\!CH_2\!-\!\overset{O}{\overset{\diagup\diagdown}{CH}}\!-\!CH_2$ | −13.1 (c = 0.8, MeOH) |

As having then described above, according to the present invention, the bifunctional liquid crystal intermediate compound is synthesized from an optically active epoxy derivative or an optically active diepoxy derivative, so that it has become possible to readily synthesize liquid crystal intermediates with various structures, having a large permanent dipole moment near an asymmetric atom and being capable of changing its length as a flexible spacer chain. Such intermediate compounds have not been hitherto obtained.

The bifunctional optically active liquid crystal intermediate compound has a high optical purity and also has a large dipole moment. Hence, the compound is useful as a starting material for a liquid crystal or polymeric liquid crystal having a high performance.

We claim:

1. A bifunctional optically active liquid crystal intermediate compound represented by the following formula (I):

$$X-Y-\underset{*}{\overset{M}{\underset{|}{C}H}}-CH_2-OH \qquad (I)$$

wherein
X represents $CH_2=CH-$, $HOCH_2-CH_2-$, $HSCH_2-CH_2-$, $HOCH_2$, $$\underset{\|}{\overset{HO\overset{}{C}-,}{O}}$$

$HOCH_2-CH=CH-$,

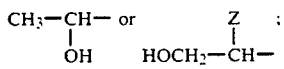

Y represents $-(CH_2)_n-$ or $-((CH_2)_m-O)_l-CH_2-$, where n represents an integer of 4 to 18, m represents an integer of 1 to 12, and l represents an integer of 1 to 4; M and Z each independently represents a halogen atom selected from the group consisting of I, Cl, Br and F; and * represents an optically active asymmetric carbon atom.

2. A bifunctional optically active liquid crystal intermediate compound represented by the following Formula (I-1):

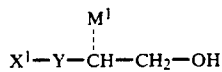

wherein
$X^1$ represents $CH_2=CH-$, $HOCH_2-CH_2-$,

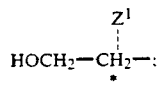

Y represents $-(CH_2)_n-$ (n=[1 to 18]4 to 18) or $-((CH_2)_m-O)l -CH_2-$ (m=1 to 12, l=1 to 4); $M^1$ and $Z^1$ may be the same or different and each represents a halogen atom; and
the mark * represents an optically active asymmetric carbon atom.

3. A bifunctional optically active liquid crystal intermediate compound according to claim 2, wherein said $M^1$ is a fluorine atom.

4. A bifunctional optically active liquid crystal intermediate compound according to claim 1, wherein said n represents an integer of 4 to 12.

5. A bifunctional optically active liquid crystal intermediate compound according to claim 1, wherein said m represents an integer of 1 to 9.

6. A bifunctional optically active liquid crystal intermediate compound according to claim 1, wherein said l represents an integer of 2 to 4.

7. A bifunctional optically active liquid crystal intermediate compound represented by the following Formula (I-1):

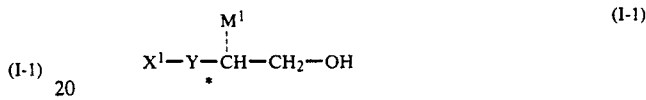

wherein
$X^1$ represents $CH_2=CH-$, $HOCH_2-CH_2-$,

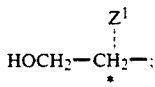

Y represents $-(CH_2)_n-$ (n=1 to 18) or $-((CH_2)_m-O)_l-CH_2-$ (m=1 to 12, l=1 to 4); $M^1$ and $Z^1$ may be the same or different and each represents a halogen atom; and
the mark * represents an asymmetric carbon atom.

8. A bifunctional optically active liquid crystal intermediate compound according to claim 7, wherein said $M^1$ is a fluorine atom.

* * * * *

UNITED STATES PATENT AND TRADEMARK OFFICE
CERTIFICATE OF CORRECTION

PATENT NO. : 5,171,470
DATED : December 15, 1992
INVENTOR(S) : HIROYUKI NOHIRA, ET AL.

It is certified that error appears in the above-identified patent and that said Letters Patent is hereby corrected as shown below:

On the title page:

IN [75] INVENTORS

"51-5,, Ohkuboryoke, Urawa-shi, Saitama-ken;" should read --Urawa--.

IN [30] FOREIGN APPLICATION PRIORITY DATA

"1-192927" should read --2-192927--.

COLUMN 1

Line 40, "Lagewall" should read --Lagerwall--.

COLUMN 3

Line 4, "Optically" should read --optically--.

COLUMN 5

Line 29, "HOCH$_2$—," should read --HOCH$_2$—, HOC—, -- 

COLUMN 6

Line 12, "journal" should read --Journal--.

COLUMN 8

Line 48, "Formula (II 2)" should read --Formula (II-2)--.
Line 51, "Niotechnology" should read --Biotechnology--.

UNITED STATES PATENT AND TRADEMARK OFFICE
CERTIFICATE OF CORRECTION

PATENT NO. : 5,171,470
DATED : December 15, 1992
INVENTOR(S) : HIROYUKI NOHIRA, ET AL.

It is certified that error appears in the above-identified patent and that said Letters Patent is hereby corrected as shown below:

COLUMN 13

Line 25, "mixture." should read --mixture,--.

COLUMN 14

Example 4, "(c = 018," should read --(c = 0.8,--.

COLUMN 15

Line 57, "of of" should read --of--.

COLUMN 16

Line 35, "then" should read --been--.

COLUMN 17

Line 32, "(n = [1 to 18]4 to 18)" should read --(n = 4 to 18)--.

UNITED STATES PATENT AND TRADEMARK OFFICE
CERTIFICATE OF CORRECTION

PATENT NO. : 5,171,470
DATED : December 15, 1992
INVENTOR(S) : HIROYUKI NOHIRA, ET AL.

It is certified that error appears in the above-identified patent and that said Letters Patent is hereby corrected as shown below:

<u>COLUMN 17</u>

Line 33, "O)1" should read --$O)_1$--.

Signed and Sealed this

First Day of March, 1994

Attest:

BRUCE LEHMAN

Attesting Officer     Commissioner of Patents and Trademarks